(12) United States Patent
Chabanas et al.

(10) Patent No.: US 9,320,421 B2
(45) Date of Patent: Apr. 26, 2016

(54) METHOD OF DETERMINATION OF ACCESS AREAS FROM 3D PATIENT IMAGES

(75) Inventors: Laurence Chabanas, Saint-Pierre-d'Allevard (FR); Stéphane Lavallee, Saint-Martin-d'Uriage (FR)

(73) Assignee: SMITH & NEPHEW, INC., Memphis, TN (US)

( * ) Notice: Subject to any disclaimer, the term of this patent is extended or adjusted under 35 U.S.C. 154(b) by 427 days.

(21) Appl. No.: 13/704,473

(22) PCT Filed: Jun. 16, 2011

(86) PCT No.: PCT/IB2011/001685
§ 371 (c)(1),
(2), (4) Date: Dec. 14, 2012

(87) PCT Pub. No.: WO2011/158115
PCT Pub. Date: Dec. 22, 2011

(65) Prior Publication Data
US 2013/0096373 A1    Apr. 18, 2013

Related U.S. Application Data

(60) Provisional application No. 61/355,210, filed on Jun. 16, 2010.

(51) Int. Cl.
*A61B 1/00*    (2006.01)
*A61B 1/317*   (2006.01)
(Continued)

(52) U.S. Cl.
CPC ............... *A61B 1/317* (2013.01); *G06T 7/0046* (2013.01); *A61B 19/50* (2013.01); *G06T 2207/10072* (2013.01); *G06T 2207/30008* (2013.01)

(58) Field of Classification Search
CPC ..... A61B 19/50; A61B 1/317; A61B 19/5244; G06T 2207/10072; G06T 2207/30008; G06T 7/0046
See application file for complete search history.

(56) References Cited

U.S. PATENT DOCUMENTS 5,995,738 A   11/1999  DiGioia et al.
7,672,709 B2  3/2010   Lavallee et al.
(Continued)

FOREIGN PATENT DOCUMENTS

JP   2009014454 A   1/2003
JP   2009082444 A   4/2009
JP   2009273521     11/2009

OTHER PUBLICATIONS

Jan et al ("Atlas-based segmentation of bone structures to support the virtual planning of hip operations", International Journal of Medical Informatics, Elsevier, vol. 64, Dec. 2001, pp. 439-447).*
(Continued)

*Primary Examiner* — Amara Abdi
(74) *Attorney, Agent, or Firm* — Burns & Levinson LLP; Joseph M. Maraia

(57) ABSTRACT

Method of determination of access areas from 3D patient images The invention relates to a method for automatically determining at least one pre-operative portal for arthroscopy from acquired pre-operative medical images of a bone of a patient, the method comprising the following steps: i) constructing a 3D surface(S) of the bone from the 3D image of the bone; ii) determining anatomical landmarks of the bone from the 3D surface; iii) determining a bone reference coordinate system (Rbone); iv) selecting at least one predetermined portal in a database of positions of predetermined portals; v) determining a transform between the bone reference coordinate system (Rbone) and the model coordinate system (Ratlas) so that the bone of the patient and the bone of the reference person are matched in size, in position and/or shape; vi) inferring from the transform and the at least one predetermined portal the pre-operative portal.

17 Claims, 12 Drawing Sheets

(51) Int. Cl.
*G06T 7/00* (2006.01)
*G06K 9/00* (2006.01)
*A61B 19/00* (2006.01)

(56) References Cited

U.S. PATENT DOCUMENTS

| | | | |
|---|---|---|---|
| 2003/0109780 A1 | 6/2003 | Coste-Maniere et al. | |
| 2005/0143676 A1 | 6/2005 | De Guise et al. | |
| 2007/0122233 A1 | 5/2007 | Maier et al. | |
| 2007/0195933 A1 | 8/2007 | Bogojevic et al. | |
| 2007/0249967 A1* | 10/2007 | Buly | A61B 5/1121 600/595 |
| 2007/0270680 A1* | 11/2007 | Sheffer | A61B 19/52 600/407 |
| 2008/0086150 A1 | 4/2008 | Mathis et al. | |
| 2008/0177173 A1 | 7/2008 | Deffenbaugh et al. | |
| 2008/0214960 A1 | 9/2008 | Hodgson et al. | |
| 2008/0312663 A1 | 12/2008 | Haimerl et al. | |
| 2008/0319449 A1 | 12/2008 | Tuma et al. | |
| 2009/0017430 A1 | 1/2009 | Muller-Daniels et al. | |
| 2009/0089034 A1 | 4/2009 | Penney et al. | |
| 2009/0112214 A1 | 4/2009 | Philippon et al. | |
| 2009/0285465 A1 | 11/2009 | Haimerl et al. | |
| 2010/0049493 A1 | 2/2010 | Haimerl | |
| 2011/0190774 A1* | 8/2011 | Nikolchev | A61B 17/56 606/90 |

OTHER PUBLICATIONS

Subburaj et al ("Automated identification of anatomical landmarks on 3D bone models reconstructed from CT scan images", Computerized Medical Imaging and Graphics 33, 2009 Elsevier, pp. 359-368).*
Kudiak et al ("Range of Motion in Anterior Femoroacetabular Impingement", Clinical Orthopedics and related research No. 458; pp. 117-124, 2007 Lippincott Williams and Wilkins).*
Tannast et al ("Computer-assisted Simulation of Femoro-acetabular Impingement Surgery", Navigation and MIS in Orthopaedic Surgery, Berlin, Heidelberg, New York: Springer-Verlag pp. 448-455, 2006).*
Dudda M. et al, "Do Normal Radiographs Exclude Asphericity of the Femoral Head-Neck Junction?", Clin Orthop Relat Res (2009) 467:651-659.
Rakhra K.S. et al, "Comparison of MRI Alpha Angle Measurement Planes in Femoroacetabular Impingement", Clin Orthop Relat Res (2009) 467:660-665.
Kang et al, "Accurate simulation of hip joint range of motion", Computer Animation Conference—CA, pp. 215-219, 2002.
Brunner A. et al, "Evaluation of a Computed Tomography—Based Navigation System Prototype for Hip Arthroscopy in the Treatment of Femoroacetabular Cam Impingement", Arthroscopy: The Journal of Arthroscopic and Related Surgery, vol. 25, No. 4 Apr. 2009: pp. 382-391.
Arbabi E. et al, "A fast method for finding maximum range of motion in the hip joint", CAOS 2007, Heidelberg, Germany, p. 20-23.
Arbabi E. et al, "Penetration Depth Method—Novel Real-Time Strategy for Evaluating Femoroacetabular Impingement", Journal of Orthopaedic Research, vol. 28, Issue 7, pp. 880-886, Jul. 2010.
Dario P. et al, "A Novel Mechatronic Tool for Computer-Assisted Arthroscopy", IEEE Engineering in Medicine and Biology Society 2000;4(1):15-29.
Hodgson A.J. et al, "Computer-assisted femoral head resurfacing", Computer Aided Surgery, Sep./Nov. 2005; 10(5/6): 337-343.
Kendoff D. et al, "Feasibility of a navigated registration technique in FAI surgery", Archives of Orthopaedic and Trauma Surgery, vol. 131, No. 2, pp. 167-172, 2011.
Wengert C. et al, "Markerless Endoscopic Registration and Referencing", Med Image Comput Comput Assist Interv. 2006;9(Pt 1):816-23.
Monahan E. et al, "Computer-aided navigation for arthroscopic hip surgery using encoder linkages for position tracking", Int J Med Robotics Comput Assist Surg 2006; 2: 271-278.
Monahan E. et al, "A study of user performance employing a computer-aided navigation system for arthroscopic hip surgery", Int J CARS (2007) 2:245-252.
Charbonnier C. et al, "Motion study of the hip joint in extreme postures", The Visual Computer, vol. 25, No. 9, pp. 873-882, 2009.
Gilles B. et al, "MRI-based Assessment of Hip Joint Translations", J Biomech, vol. 42, Jun. 2009.
Murphy S.B. et al, "Arthroscopic percutaneous computer assisted FAI relief using a new method of CT-fluoro registration", Computer-Assisted Orthopedic Surgery-International, 2007.
Barrett A.R.W et al, "Preoperative planning and intraoperative guidance for accurate computer-assisted minimally invasive hip resurfacing surgery", Proc. IMechE vol. 220 Part H, 2006.
Puls M. et al, "Simulation of Hip Motion for Impingement Detection: A Comparison of Four Strategies", Journal of Biomechanics 41(S1), 16th ESB Congress, Oral Presentations, Tuesday Jul. 8, 2008.
Cai D. et al, "Rapid Impingement Detection System with Uniform Sampling for Ball-and-Socket Joint", Workshop on 3D Physiological Human, Zermatt, Switzerland, Dec. 1-4, 2008.
Tannast M. et al, << Computer-assisted Simulation of Femoro-acetabular Impingement Surgery >>, In JB Stiehl, WH Konermann, RG Haaker, AM DiGioia (eds.): "Navigation and MIS in Orthopaedic Surgery", Berlin, Heidelberg, New York: Springer-Verlag. pp. 448-455, 2006.
Tannast M. et al, "Noninvasive three-dimensional assessment of femoroacetabular impingement", Journal of Orthopedic Research, Jan. 2007.
Wu C., "3D Reconstruction and Tracking of Anatomical Structures from Endoscopic Images", Thesis, 2009.
Charbonnier C. et al, "Virtual Hip Joint: from Computer Graphics to Computer-Assisted Diagnosis", Eurographics 2009, Mar. 30-Apr. 3, Munich, Germany.
Ehrhardt J et al: "Atlas-based segmentation of bone structures to support the virtual planning of hip operations", International Journal of Medical Informatics, Elsevier Scientific Publishers, Shannon, IR, vol. 64, No. 2-3, Dec. 1, 2001, pp. 439-447, XP004329229.
Fritscher K D et al: "Model guided diffeomorphic demons for atlas based segmentation",Proceedings of the SPIE—The International Society for Optical Engineering SPIE—The International Society for Optical Engineering USA, vol. 7623, Feb. 14, 2010, pp. 1-8, XP008155589.
Bond J L et al: "The 23-Point Arthroscopic Examination of the Hip: Basic Setup, Portal Placement, and Surgical Technique", Arthroscopy, Raven Press, New York, NY, US, vol. 25, No. 4, Apr. 1, 2009, pp. 416-429, XP026070349, J.ARTHR0.2008.08.021 [retrieved on Nov. 22, 2008].
Lisa Gottesfeld Brown: "A Survey of Image Registrati0n Techniques", ACM Computing Surveys, ACM, New York, NY, US, US, vol. 24, No. 4, Dec. 1, 1992, pp. 325-376, XP001006912.
International Search Report for Internatonal Application No. PCT/IB2011/001685.
Office Action for EP Patent Application No. 11764608.3-1502, dated Oct. 11, 2013, 5 pages.
Office Action for Australian Patent Application No. 2011266778 dated May 15, 2014, 3 pages.
Notice of Reasons for Rejection Office Action and English Translation for Japanese Patent Application No. 2013-514800 dated Apr. 6, 2015, 4 pages.
Zaragoza, E.J. "3D CT and the Imaging Approach to Femoroacetabular Impingement Syndrome", Section 4, Orthopedic Imaging, TeraRecon Clinical Case Studies—vol. 1, pp. 143-150, downloaded from http://int.terarecon.com/literature/clinical-case-studies/clinical-case-studies-volume-1, Jan. 8, 2016.

* cited by examiner

METHOD OF DETERMINATION OF ACCESS AREAS FROM 3D PATIENT IMAGES

TECHNICAL FIELD

The invention relates to the field of computer assisted surgery, and more particularly to a method for determining portals for arthroscopy.

BACKGROUND OF THE INVENTION

Articulations of the human body are often very complex systems and no precise generic model exists to capture all the variability from one articulation to another. It is therefore necessary to use specific medical images or collection of digital patient data in order to get relevant information to develop techniques, devices and methods that will facilitate a treatment or a diagnosis. Our description focuses on the hip articulation between the acetabulum and the proximal femur although it can be easily extended to other articulations such as shoulder for example.

Structural abnormalities in the morphology of the hip can limit motion and result in repetitive impact of the proximal femoral neck against the acetabular labrum and its adjacent cartilage. Femoro Acetabular Impingement (FAI) is a pathology that can result from a decreased femoral head-neck offset (cam effect), an overgrowth of the bony acetabulum (pincer effect), excessive acetabular retroversion or excessive femoral anteversion, or a combination of these deformities. The cam impingement is generally characterized by a bone overgrowth located at the antero-superior aspect of the femur head-neck junction, which destructures the spherical shape of the femur head. The pincer impingement is generally characterized by an overcoverage located at the anterior aspect of the acetabulum rim. However, the correct and full diagnosis of this pathology is not easy to determine, especially when dealing with subtle deformities. Standard radiographic X-rays are used for the initial diagnosis and then three dimensional (3D) Computed Tomography (CT) scans or Magnetic Resonance Imaging (MRI) exams are generally performed in case of suspected FAI pathology. The processing of the 3D image remains a laborious manual task which cannot ensure accuracy and reproducibility, potentially misleading the diagnosis or the surgical indication. Moreover, even though 3D information can be extracted from such exams, the reconstructed bone volumes remain static and cannot predict with reliability the exact location of the impingement which occurs during the mobilization of the hip.

The surgical treatment of FAI aims at restoring a normal spherical shape to the femur head at the level of the bony cam lesion and restoring a normal coverage rate of the acetabular rim at the level of the pincer lesion, by removing the excess of bone. The result of this bony reshaping is the restoration of a greater range of motion of the hip, without impingement. Conventionally, the open surgical approach had initially been adopted since it provides a full exposure of the bone and direct access to the anatomy to be treated. Though, since minimally invasive procedures have grown in popularity by reducing the pain, morbidity and recovery time for patient, arthroscopic treatment of FAI has been explored in the last decade, which requires the use of an endoscopic camera and specific small instruments that can pass through various types of canulas. Advantages include minimally invasive access to the hip joint, peripheral compartments, and associated soft tissues. Furthermore, arthroscopy allows for a dynamic, intra-operative assessment and correction of the offending lesions. However, due to the depth of the joint and the reduced visibility and access, theses hip arthroscopy procedures are difficult to perform and not all surgeons feel comfortable about adopting the technique. The success of such arthroscopic interventions relies on a very meticulous intra-operative evaluation and a thorough and accurate correction of impingement lesions on both the femoral and acetabular sides, which can only be accomplished after a laborious learning curve over many cases. Failure of arthroscopic procedures for FAI is most commonly associated with incomplete decompression of the bony lesions. Another negative aspect of the arthroscopic procedures for FAI is the intensive use of intra-operative fluoroscopy imaging system to augment the visual control from the endoscopic camera by X-ray images. The fluoroscopic control enables a better localization of the instruments and assessment of the current correction, at the expense of high radiation exposure for the patient and the OR personnel.

Computer assisted surgical procedures have now been used in orthopedic surgery for over twenty years, in order to help the surgeon in performing the surgery with better accuracy and reproducibility. The main principle of computer assisted surgery and surgical navigation in particular is the tracking of surgical instruments relatively to the patient anatomy to guide the surgeon in order to achieve a precise target. Generally, a surgical navigation system includes a localization device, at least one tracker and a processor. One or more emitters are embedded in either the localization device or the tracker. One or more receivers are embedded in the other of the localization device or the tracker to detect the signals emitted by the emitters. The signals are transmitted to the processor, which computes localization data to detect the relative position and orientation of the tracker and localization device. Usually, three degrees of freedom are determined for the translation component of a tracker and three degrees of freedom for the rotation component. It is known that the localization device of a surgical navigation system can use several types of signals: optical, electromagnetic, ultrasonic, or other, depending on the most appropriate technology to be compatible with the surgical environment. Most commonly, passive reflective markers constitute trackers that are observed by a pair of stereoscopic camera that constitute the localization device. In other standard systems, emitters are made of infra-red LEDs and they are observed by at least three linear CCD cameras having cylindrical lenses. It is also common to use electromagnetic technology: one or several emitter coils constitute the localization device and several miniature coils constitute the trackers that can be attached to instruments or directly to the bones; miniature coils can track the full six degrees of freedom of a solid or reduced versions can track only five degrees of freedom (position of a point and orientation of an axis). Generally in orthopedic navigated surgery, at least one tracker is rigidly attached to the patient anatomy which is undergoing the surgical procedure, for example a bone, usually with a broach or pin mechanism. And at least one tracker is attached to a surgical instrument, for which the part to be tracked is calibrated, for example the tip of a drill. The localization device and the tracker are linked to the computer processor on which software is running to record trackers positions, register patient data and compute instruments trajectories.

The patient data may be obtained from several sources, either from pre-operative data such as 3D image from computer tomography (CT) scans or magnetic resonance (MR) exams for example, or from intra-operative digitization of the anatomy such as bone surface points digitization to build a bone surface model from statistical deformation of a reference model. The software of the navigation system processes patient data and according to the specific goal will generally compute an optimized trajectory or position for a surgical instrument, a cutting jig for example. Intra-operatively, the tracked instrument needs to be localized relatively to the patient anatomy. If the patient data is directly obtained from intra-operative anatomy digitization then both the patient reference system and the instrument reference system are known in the same coordinates system via the localization device, and the instrument can be directly navigated relatively to the patient data. However, in minimally invasive (MIS) procedures such as arthroscopy, the patient anatomy access is generally reduced and cannot allow for a direct digitization of the anatomy. Usually in such cases, intra-operative images such as fluoroscopy X-rays or endoscopic images are used to obtain intra-operative data. But in cases such as hip arthroscopy, 2D image information is generally not sufficient to achieve the required accuracy in three dimensions, and a pre-operative 3D image is usually required.

If the patient data is obtained from a pre-operative acquisition, an intermediate process needs to be performed before the navigation of the instrument relatively to the patient data. It is called registration, in order to match the pre-operative data of the patient to the reference system of the actual patient installed for surgery. This known procedure can be performed with a variety of different methods. It requires the acquisition of intra-operative patient data to be matched with the pre-operative patient data. The registration process can be based on specific paired points which are anatomical or fiducial points identified in the pre-operative data and matched with the same points digitized intra-operatively. The registration can also be based on image similarity measures between pre-operative image volume and intra-operative fluoroscopic image, using maximization of entropy, mutual information, or correlation coefficients for example. In the case of intra-operative image acquisition, the imaging system needs to be linked to the processor of the navigation system, and tracked by the localization device.

In the case of pre-operative acquisition of patient data such as CT or MR 3D image, a process is generally applied to the data to identify targets that can be anatomical structures, determine instruments trajectories or bony cutting planes or axes for example. The aim of the registration process is to be able to track the surgical instrument in the actual surgical site in accordance to a pre-operatively defined target. In all cases mentioned above, the surgical instrument can be also attached to the extremity of a robot or a haptic device that constrains the motions of the surgeon tool.

To use and apply these computer assisted surgery or navigation concepts to hip arthroscopy surgical procedures would provide a powerful solution to the problems stated earlier. In order to provide the arthroscopy surgeon with the most appropriate tool to help him/her achieving the optimal surgical result, specific computer assisted surgical devices and techniques have to be created to adapt to the specificity of hip arthroscopy environment and constraints.

From the issues described above, it can be easily understood that new specific devices and methods are needed to answer the problems and needs of hip arthroscopy surgeons, from the diagnosis and pre-operative planning to the actual surgical action.

SUMMARY OF THE INVENTION

The invention provides a method for automatically determining at least one pre-operative portal for arthroscopy from acquired pre-operative medical images of a bone of a patient, the method comprising the following steps:

i) constructing a 3D surface of the bone from the 3D image of the bone;
ii) determining anatomical landmarks of the bone from the 3D surface;
iii) determining a bone reference coordinate system from the anatomical landmarks;
iv) selecting at least one predetermined portal in a database of positions of predetermined portals previously defined on a 3D model representing a bone of a reference person;
v) determining a transform between the bone reference coordinate system and the model coordinate system so that the bone of the patient represented in the bone reference coordinate system and the bone of the reference person represented in the model coordinate system are matched in size, in position and/or shape;
vi) inferring from the transform and the at least one predetermined portal the pre-operative portal.

Another object of the invention is a method for simulating arthroscopic images before surgery, comprising the steps of determining at least one pre-operative portal by the method according to claim 1, placing a virtual arthroscope at said pre-operative portal and computing a virtual arthroscopic image of the surgical area obtained by the virtual arthroscope.

The pre-operative portal is preferably an arthroscopic portal defined by a tool entry point and a direction.

According to an advantageous embodiment of the invention, the method comprises inferring through the transform critical areas containing vessels or nerves from the model coordinate system to the bone reference coordinate system.

The transform may be determined through analytical and/or geometric process.

The transform may be determined as a continuous function from the model coordinate system to the bone reference coordinate system.

In particular, the transform may be determined through a non-rigid image-to-image or surface-to-surface registration algorithm.

In the simulation method according to the invention, the pre-operative portal may be an arthroscopic portal defined by a tool entry point and a direction, and a virtual arthroscopic image may thus be constructed from the arthroscopic portal.

Said method may further comprise generating planning information and superimposing the planning information onto the virtual arthroscopic image.

According to an embodiment, the planning information is a color map representing amount of bone to be removed.

According to another embodiment, the planning information is a projection of an optimal surface to be built onto the bone.

In addition, said method may further comprise generating an adjusted virtual arthroscopic image by adjusting and registering the virtual arthroscopic image to real arthroscopic image of the bone.

Registering the virtual arthroscopic image to real arthroscopic image of the bone preferably comprises the following steps:

i) initial registration by using the inferred portal position;
ii) adjustment of registration using image to image registration.

The method may further comprise generating planning information and generating a superimposed image by superimposing the planning information onto the adjusted virtual arthroscopic image.

According to an embodiment, the method comprises generating planning information and superimposing planning information and the adjusted virtual arthroscopic image onto the real arthroscopic image of the bone.

The method may advantageously comprise displaying the superimposed image and the real arthroscopic image side by side.

Preferably, the method comprises the manual modification of the pre-operative portal around its initial computed position.

DETAILED DESCRIPTION OF THE INVENTION

The following description is directed to the use of CT images but it can be easily extended to other 3D images such as MR images.

The purpose of the invention is to provide a method and a device for helping the user to accurately and automatically determine portals and safe access areas for arthroscopic procedures using pre-operative 3D image and also for planning relevant arthroscopic images that can be used during the surgery in addition to target data. It is intended to provide a very simple and fast rehearsal tool or simulation of surgery. Moreover, the invention provides help for the surgeon to locate and use the predefined portals and safe access areas during surgery.

For clarity, an example of the method of the invention is described for the femur and pelvis bones during a hip arthroscopy procedure in the case of a FAI indication, but it can be applied to any other human or animal bone for which itself or the adjacent ligaments, tendons and muscles present an abnormality and for which an arthroscopic procedure has to be performed, for instance in the case of knee anterior cruciate ligament repairs or shoulder rotator cuff repairs.

From the patient 3D image, an external 3D surface model S of the bone showing the cortical surface or the cartilage surface is reconstructed. This can be achieved using a variety of methods, for instance by using conventional segmentation techniques with simple thresholding followed by conventional mathematical morphology algorithms. It is possible to use the well known marching cube algorithms or the dividing cube algorithms. On MR images, the most elementary method is the delineation of contours using a mouse and active contouring using snakes. Snakes are curves like spline or Bezier curves controlled by a few control points on which a function is applied that generates forces in the direction of image gradients for instance, so that locally it will fit contours and globally it needs assistance from the user to displace the control points.

Figure 1:
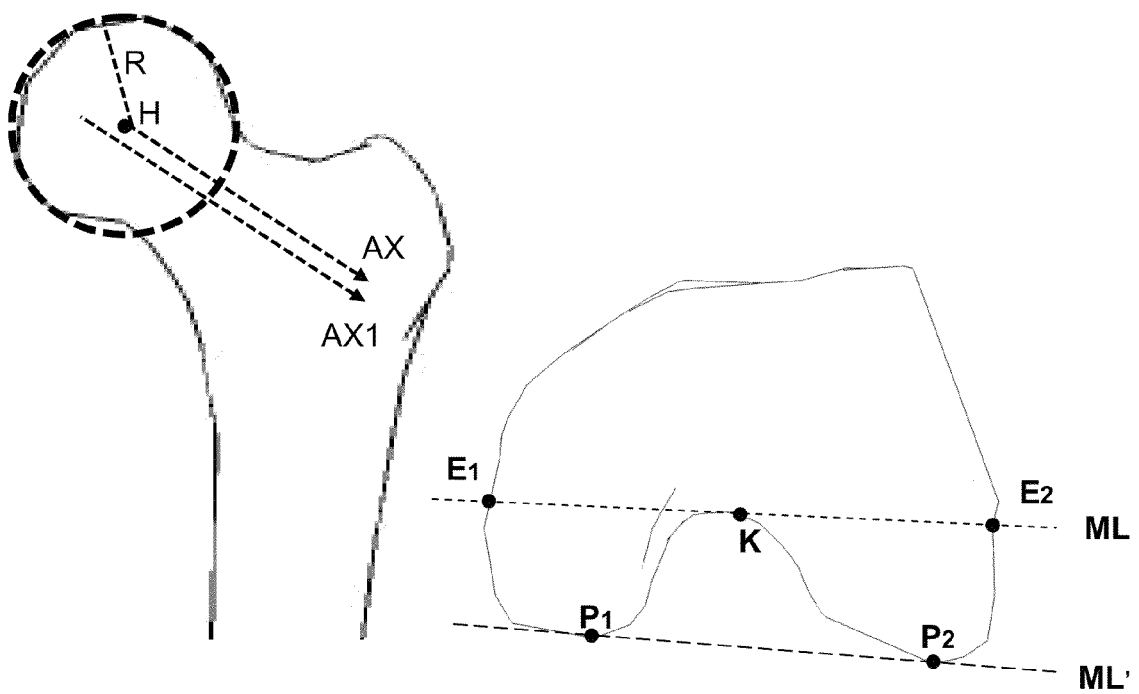
FIG. 1 is a perspective view of parts of a femur bone with anatomical landmarks

From a particular bone surface S and the 3D image, it is possible to determine anatomical landmarks (points and axis) that represent critical geometrical reference elements. As shown on FIG. 1, in the case of the femur, the center of the femoral head H and the radius R of the sphere that best approximate the femoral head have been determined in a step that precedes the use of the method of the invention. Likewise, an axis AX that best approximates the neck axis has been determined. More precisely, the true neck axis AX1 does not pass necessarily through the head center H and therefore we define the neck axis AX as the axis passing through H and parallel to the true neck axis. Likewise, the knee center K of the femur has been determined on the 3D image, together with a medio-lateral axis ML that can be the line joining the epicondyles E1 and E2 or another definition ML' is the line joining the most posterior points P1 and P2. An elementary method for determining those landmarks is simply an interactive delineation on the 3D image using a mouse which is commonly performed for difficult cases. But automatic method can also be applied using dedicated algorithms for detection of a sphere, a neck, a landmark point and the like. The invention can be implemented whatever the method for obtaining the anatomical landmarks is.

Figure 2:
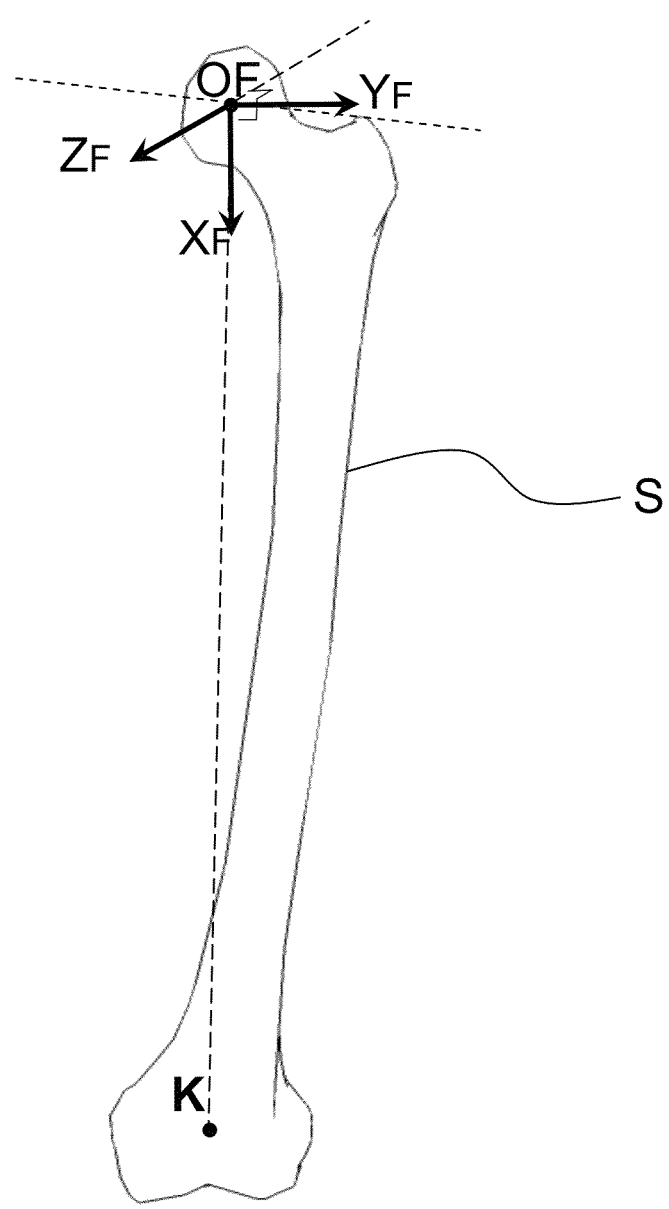
FIG. 2 is a perspective view of a complete femur bone with anatomical landmarks

From the anatomical landmarks, a bone reference coordinate system Rbone=(OF, $X_F$, $Y_F$, $Z_F$) is determined for the femur according to the following method, as illustrated in FIG. 2. In a preferred embodiment, the origin $O_F$ of the femur reference coordinate system is the point H. The $X_F$ direction is the line (HK) between the hip center H and the knee center K. The normalized vectorial product between $X_F$ and AX defines the vector $Z_F$. The vectorial product between $Z_F$ and $X_F$ defines the vector $Y_F$. The femur reference coordinate system Rbone is then entirely defined. In another embodiment, the same method is applied but the neck axis AX is replaced by the medio-lateral axis ML or ML'.

Figure 3:
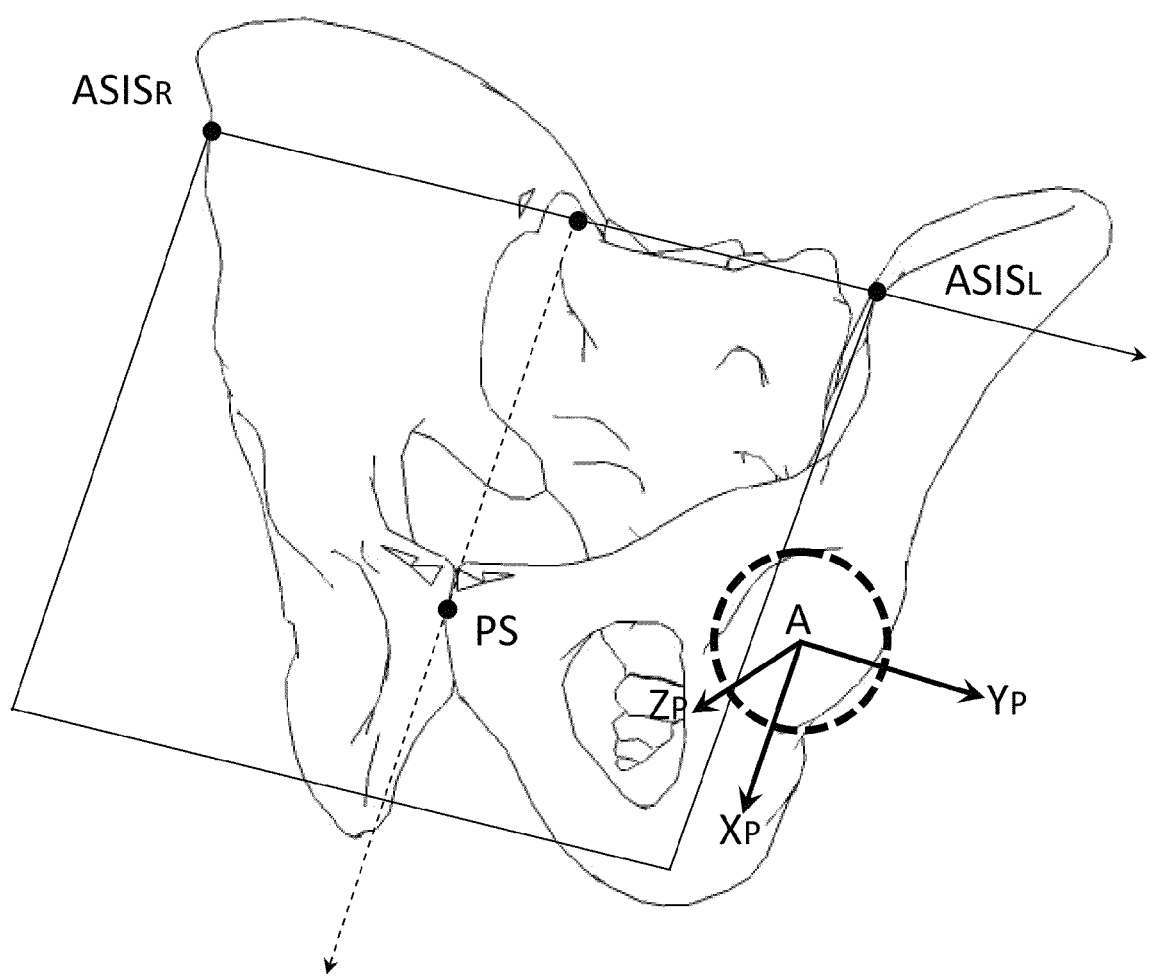
FIG. 3 is a perspective view of a complete pelvis bone with anatomical landmarks
Figure 4:
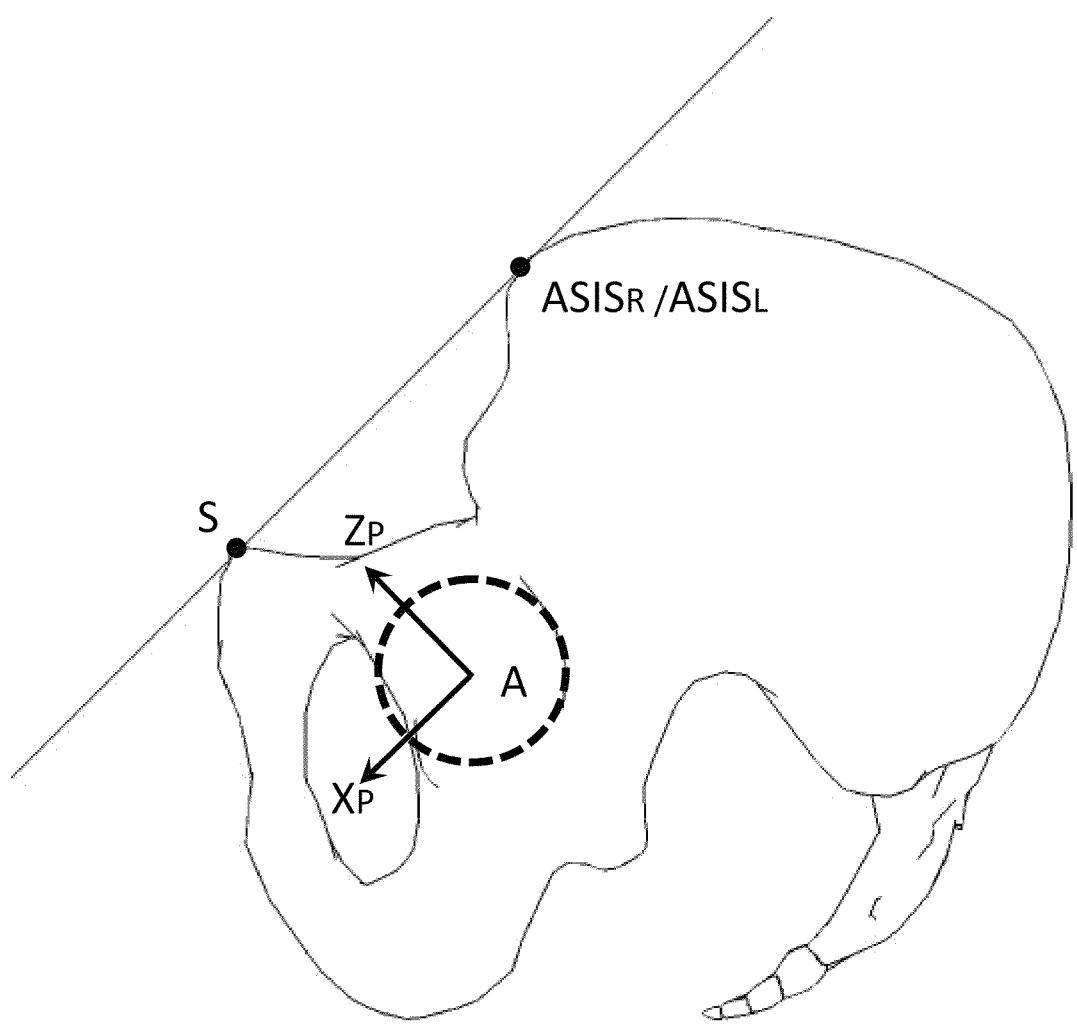
FIG. 4 is a perspective side view of a complete pelvis bone with anatomical landmarks

Another example is given for the pelvis bone, as illustrated on FIG. 3 and FIG. 4. On the pelvis side, the bone reference coordinate system is constructed from 4 anatomical landmarks: the pubis symphysis PS, the left and right antero-superior iliac spines $ASIS_L$ and $ASIS_R$, and the center of the acetabulum sphere A. Our protocol requires the acquisition of a few CT slices at the level of the iliac spines, which is usually contained in a separate file in a standard DICOM format (which is well known in the medical field) but with the same coordinates for all files that constitute sub-volumes of the 3D image. Our process identifies the $ASIS_L$ and $ASIS_R$ points automatically. The detection of the most anterior points on the left and right side of the 3D image is performed by searching those points in the 3D image. The pubic symphysis PS can also be automatically detected, by searching for a plane passing through $ASIS_L$ and $ASIS_R$ and rotating around the axis made by those 2 points until it hits the most anterior point PS outside of a vicinity of two centimeters around $ASIS_L$ and $ASIS_R$. The acetabulum sphere centered in the point A is computed from an initial estimate which comes from the femoral head sphere H computed earlier for the femur. For example, the femoral head sphere can be dilated by an average cartilage thickness of 5 mm, and then closest surface points are searched this time in the pelvis 3D surface forming a new cloud of points. A new best fitting sphere is computed from this new cloud of points. The center of the new best fitting sphere defines the acetabulum center point A. These are only examples and there can be other ways to automatically or interactively detect these anatomical landmarks. From these four points, the pelvis reference coordinate system is constructed in the following manner: the origin is the center point of the acetabulum sphere A, the $Y_P$ axis is defined as the line passing through both iliac spines, the $X_P$ axis is defined as the line orthogonal to the iliac spines axis and passing through the public symphysis PS, and the $Z_P$ axis is constructed as the vector product of $X_P$ by $Y_P$. Rbone=(A, $X_P$, $Y_P$, $Z_P$) determines the pelvis reference coordinate system.

Once a specific bone reference coordinate system Rbone has been attached to a bone using the method described above, the next step is to assign some pre-determined access elements to the patient data.

In a preliminary and parallel step, a data base is built to store the position of pre-determined access elements in the coordinate system of a 3D model. The 3D model is referred to as an atlas, it can be built manually but this is difficult. In a preferred embodiment, a 3D image ATLAS of a particular reference person that is representative of the population is selected. A model coordinate system Ratlas=(OF', $X_{F'}$, $Y_{F'}$, $Z_{F'}$) is built and attached to the bone surface model built from the particular reference person image using exactly the same method described above for the patient.

Specific access elements are determined in Ratlas. Access elements can be portals or critical areas. They constitute a database DB of access elements. Such database DB can be built using the knowledge of experts and it can be modified according to the evolution of the knowledge of experts. In a preferred embodiment, the database contains a pattern of portals. A pattern of portals is a list of N elements where each element (G',D') defines a target point G' and a direction D' that are determined using specific geometric rules. In a preferred embodiment, for the case of FAI surgery, the pattern of portals is a list of 3 elements ($G'_{Ant}$, $D'_{Ant}$), ($G'_{Ant-Lat}$, $D'_{Ant-Lat}$), ($G'_{Post-Lat}$, $D'_{Post-Lat}$) where G' Ant is the target point of the anterior portal and $D'_{Ant}$ is the direction vector of the anterior portal. $G'_{Ant-Lat}$ is the target point of the anterior lateral portal and $D'_{Ant-Lat}$ is the direction vector of the anterior lateral portal. $G'_{Post-Lat}$ is the target point of the posterior lateral portal and $D'_{Post-Lat}$ is the direction vector of the posterior lateral portal.

Figure 5:
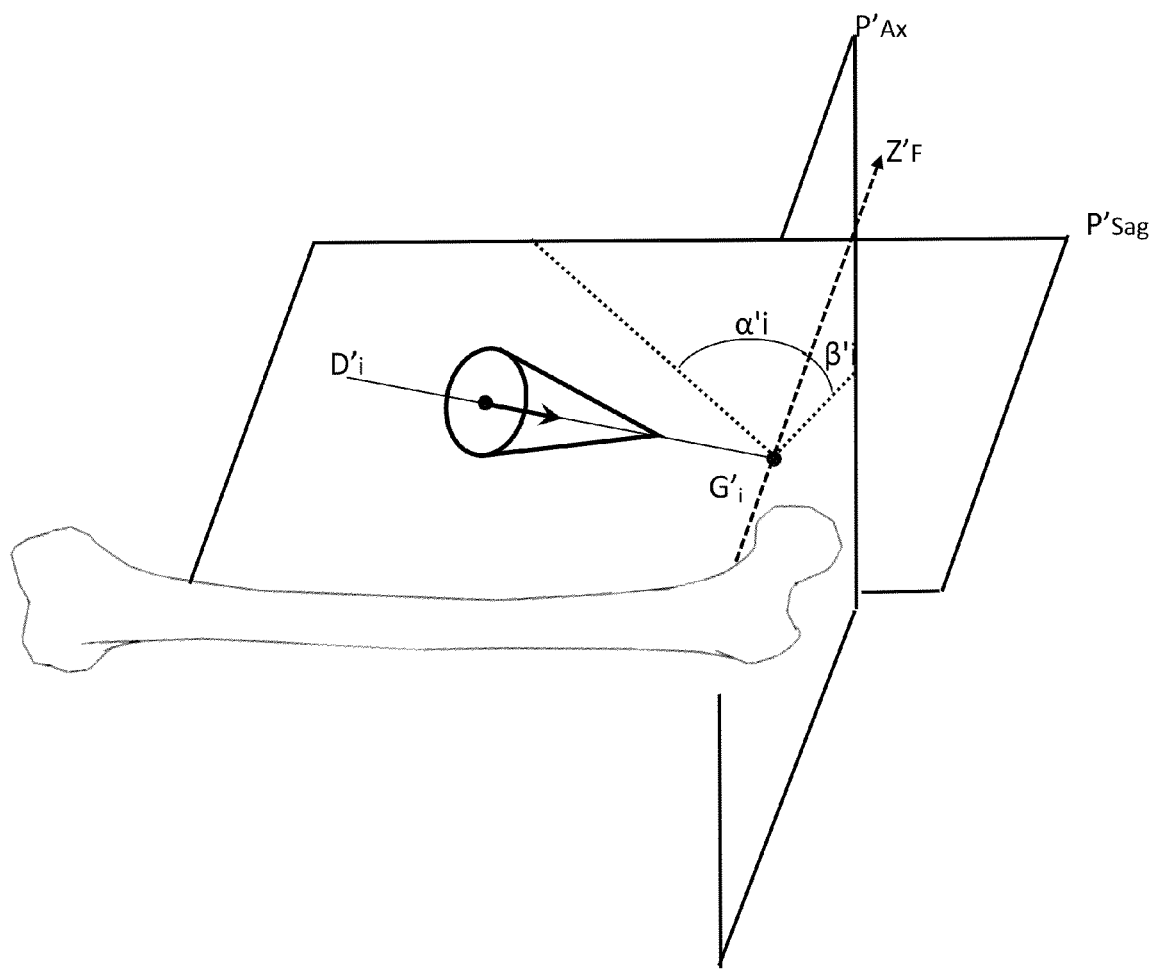
FIG. 5 is a perspective view of a femur bone with a portal
Figure 6:
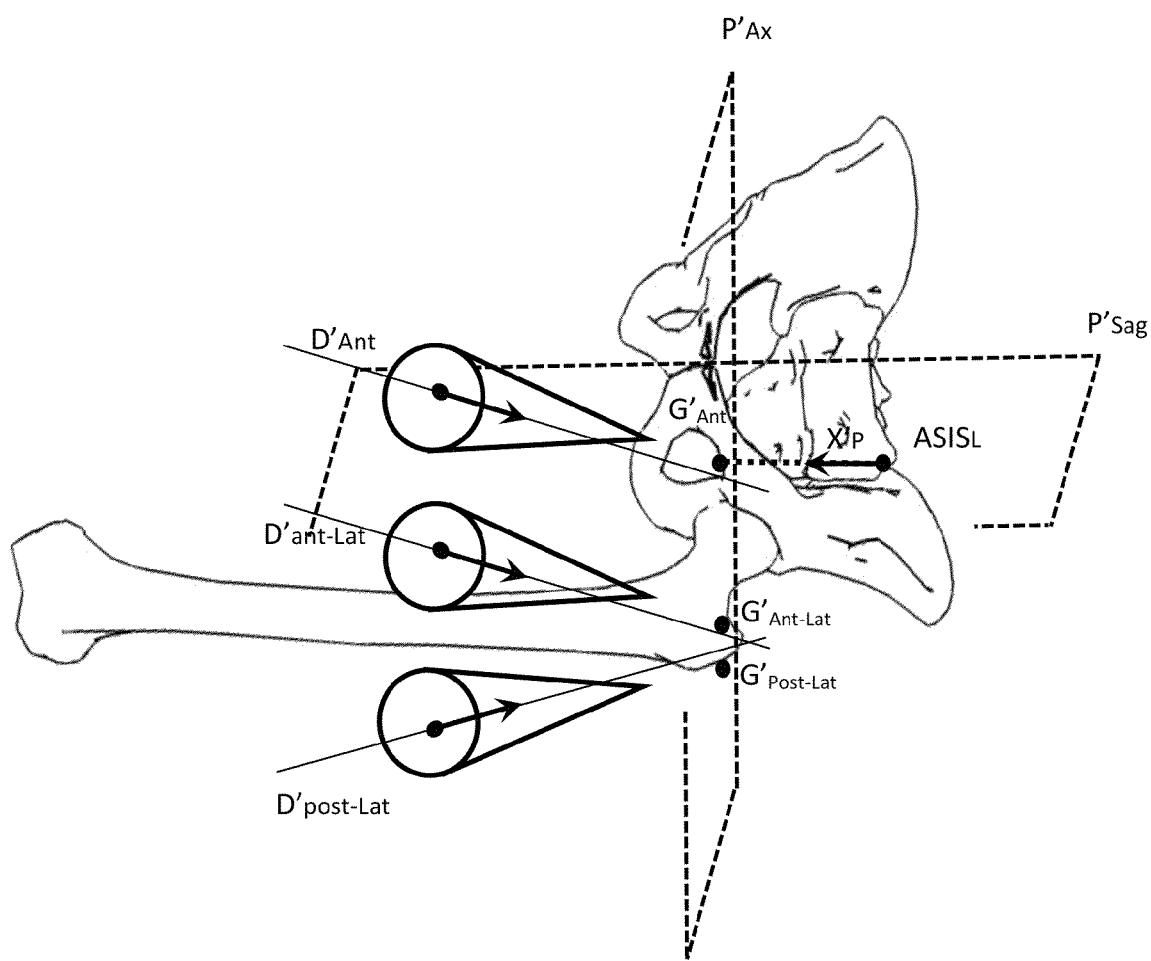
FIG. 6 is a perspective view of a femur and pelvis with 3 portals

An example of a specific pattern of portals that has been built by medical experts is described hereafter, as represented on FIG. 4 and FIG. 5. It is only one example and the invention does not aim at recommending one pattern versus another one. In this pattern, all three portals target points $G'_{Ant}$, $G'_{Ant-Lat}$, $G'_{Post-Lat}$ are lying in an axial plane $P'_{Ax}$ parallel to the ($Y'_F Z'_F$) plane of the femoral model coordinate system and passing through the superior extremity of the greater trochanter. All direction vector D'i are defined by a pair of angles ($\alpha'i$, $\beta'i$) where $\alpha'i$ is the angle measured in the sagittal plane $P'_{Sag}$, and $\beta'i$ is the angle measured in the axial plane $P'_{Ax}$, relatively to the axis $Z'_F$. To determine the anterior portal, the anterior direction vector $D'_{Ant}$ is defined by the angles $\alpha'_{Ant}=45°$ and $\beta'_{Ant}=30°$ and $G'_{Ant}$ is defined as the intersection of the plane $P'_{Ax}$ and a straight line parallel to the X'p axis of the pelvis model coordinate system and passing through the antero-superior iliac spine ASIS of the concerned hip side. To determine the anterior lateral portal, the anterior lateral direction vector $D'_{Ant-Lat}$ is defined as parallel to $D'_{Ant}$ ($\alpha'_{Ant-Lat}=45°$, $\beta'_{Ant-Lat}=30°$) and $G'_{Ant-Lat}$ is defined as the intersection of the plane $P'_{Ax}$ and a line of direction vector $D'_{Ant-Lat}$ tangent to the anterior aspect of the greater trochanter. To determine the posterior lateral portal, the posterior lateral direction vector $D'_{Ant-post}$ is defined by the angles $\alpha'_{Post-Lat}=135°$, $\beta'_{Post-Lat}=30°$, and $G'_{Post-Lat}$ is defined as the intersection of the plane $P'_{Ax}$ and a line of direction vector $D'_{Post-Lat}$ tangent to the posterior aspect of the greater trochanter. This is just an example, other patterns can be defined to describe other target points $G'_i$ and direction vectors $D'_i$. A pattern of portals can contain one or two or three or more than elements.

In an identical manner, portals can be defined relatively to acetabulum model coordinate system, or from a combination of criteria in both the femur and the acetabulum model coordinate systems.

The next step of the method is to infer the pre-determined access elements built in the atlas to the patient. This is achieved by building a transform [T] between Rbone and Ratlas. Since the same method is used for determining Ratlas and Rbone from their respective 3D image, the transform [T] can be assigned to the identity transform. However, in a preferred embodiment, a size factor is assigned in order to take into account significant variations between the atlas and the patient. We assume that the radius of the femoral head has been determined for both the patient and the atlas, it is noted R for the patient and R' for the atlas. The ratio value R/R' is computed and stored as a factor k. The transform [T] is then assigned to a scaling matrix of ratio k such that the coordinates ($x_F$, $y_F$, $z_F$) of a point in Rbone are deduced from the coordinates of a point ($x'_F$, $y'_F$, $z'_F$) in Ratlas using $x_F = k \cdot x'_F$ and $y_F = k \cdot y'_F$ and $z_F = k \cdot z'_F$. Since both Rbone and Ratlas are centered around their respective hip center H and H', this transform [T] maintains the hip center constant and just applies a scale factor to match both femoral heads. The target points G' defined in Ratlas are therefore transformed in target points G in the Rbone in a very simple and fast manner. With this method, the target points that are lying on the femoral head surface of the atlas are transformed in points lying on the femoral head surface on the patient bone. It is then assumed that landmark points are transformed into landmark points that are in the vicinity of what should be their real value. The direction vectors D remain identical to the vectors D' if they are normalized. The pattern of portals of the atlas is inferred to the patient coordinate system Rbone in a very simple, fast, automatic and robust manner. A non expert user can thus benefit from a determination of optimal portals on the basis of portal patterns which were designed by an expert.

Figure 7:
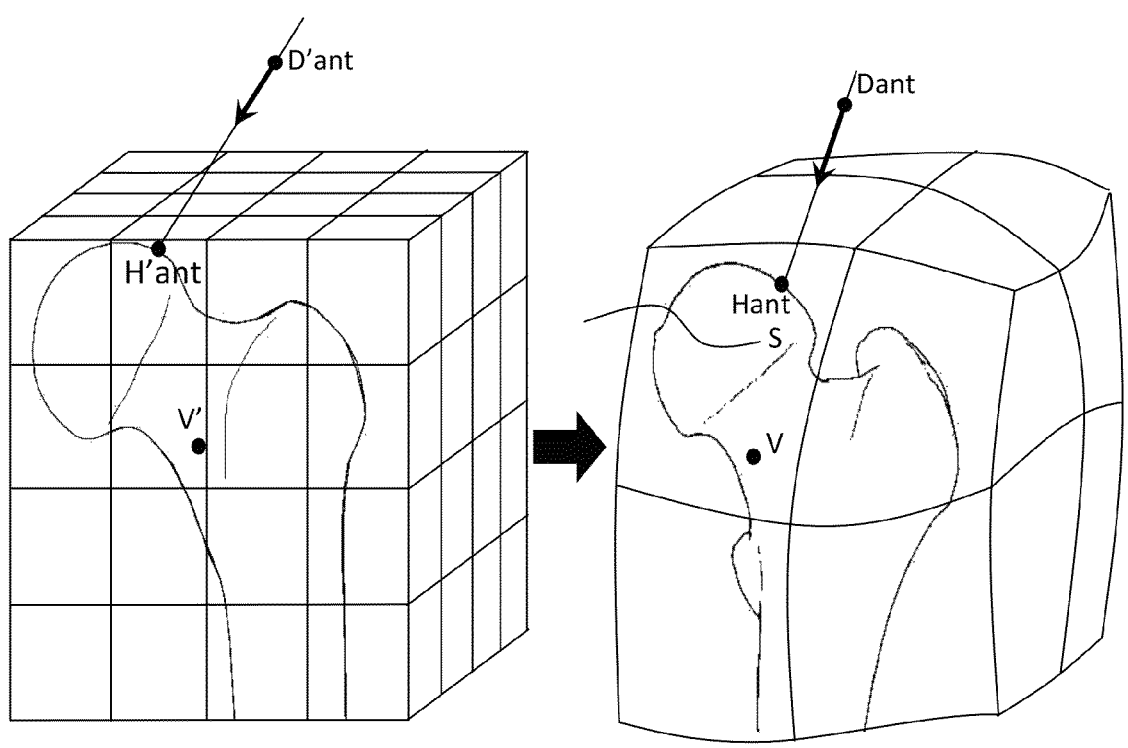
FIG. 7 is a schematic view of a grid deformation

In another embodiment, the transform [T] can be more complex than a scaling transform. A non-rigid transform [T] is built as a continuous function from Ratlas to Rbone in order to match the 3D bone surface model or directly the 3D image of the patient to respectively the model or image of the atlas. Standard non-rigid image-to-image or surface-to-surface registration algorithms can be used. The global transform from the selected predefined atlas Ratlas to the actual patient Rbone can be achieved by calculation of a deformable smooth and minimal transform between the surfaces of the predefined model and the surfaces extracted from patient data, using well known elastic surface matching algorithms. As illustrated on FIG. 7, one technique consists in calculating the deformation of a 3D mesh that is applied to the volume of the predefined model in order to match the patient model. The method is initialized using the identity matrix since Rbone and Ratlas have been determined in a similar manner and using identical definitions. Then the sum of squares of distances between the atlas surface model and the patient surface model is minimized using Levenberg-Marquardt algorithm, which results in determining displacement vectors of the mesh. In another embodiment, the 3D image of the atlas and the 3D image of the patient are registered directly by maximizing an image similarity function built from the mutual entropy, the joint correlation coefficient or other well known criteria described in the image registration literature. The advantage of this embodiment is to infer anatomical landmarks anywhere from the atlas and still maintain an accurate position of the result.

Figure 8:
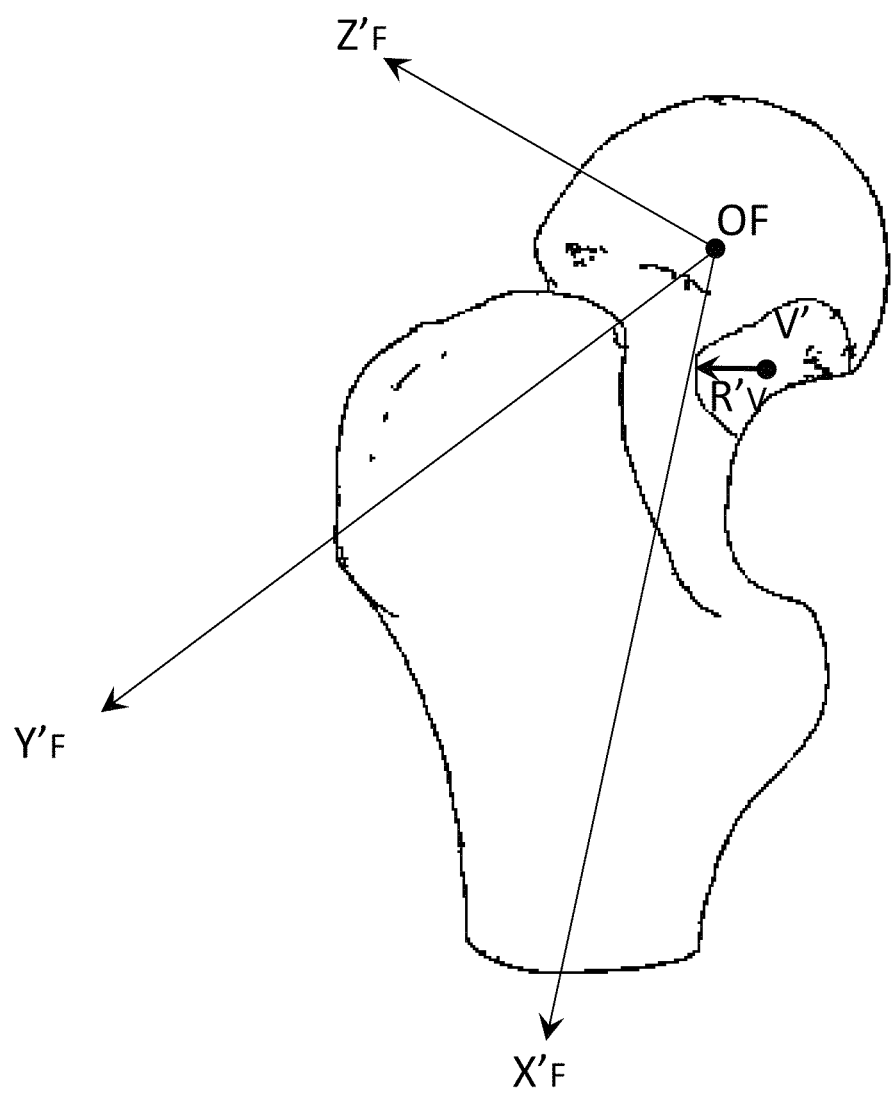
FIG. 8 is a perspective view of a femur with a dangerous area

Another characteristic element that can be inferred by this method is an area with potential risk of presence of blood vessels in the arthroscopic site. For example, it is known from the anatomical knowledge, that retinacular vessels are irrigating the bony structures lying in some precise posterior area of the femoral head neck junction. This area must be avoided during milling of the femoral head-neck area in arthroscopic procedures. As shown in FIG. 8, the method for determining this area consists in estimating a center point V' of the critical area and a radius $R'_V$ that defines the extent of the critical area in Ratlas. It determines a virtual sphere centered around V' and with a radius R'v for which the intersection with the bone surface defines the surface patch of the critical area. This area is defined in the Atlas model coordinate system Ratlas. Using the method defined previously, the point V' is transformed into a critical area point V in the patient reference coordinate system Rbone, and the radius R'v is multiplied by the k coefficient if a scaling transform [T] is used so that Rv=k·R'v. It defines a new critical area (V,Rv) that the user must avoid. If a deformable mesh is used to define the transform [T], the surface patch that defines the critical area is transformed by [T] and a new critical area is defined in the patient reference coordinate system. It is only a useful indication and warning since the method cannot guarantee the precision and accuracy of the inferred area.

More generally, any geometric construction rule known to identify anatomical characteristic elements can be used to infer targets, critical areas, access areas in the femur or in the pelvis reference coordinate system using the method defined above. It is sufficient that characteristic access elements are defined by geometric rules in the model coordinate system attached to an atlas.

The portals and critical areas determined using the method mentioned above constitute a reliable basis that any user can consider to be an initial determination of the portals.

Figure 9:
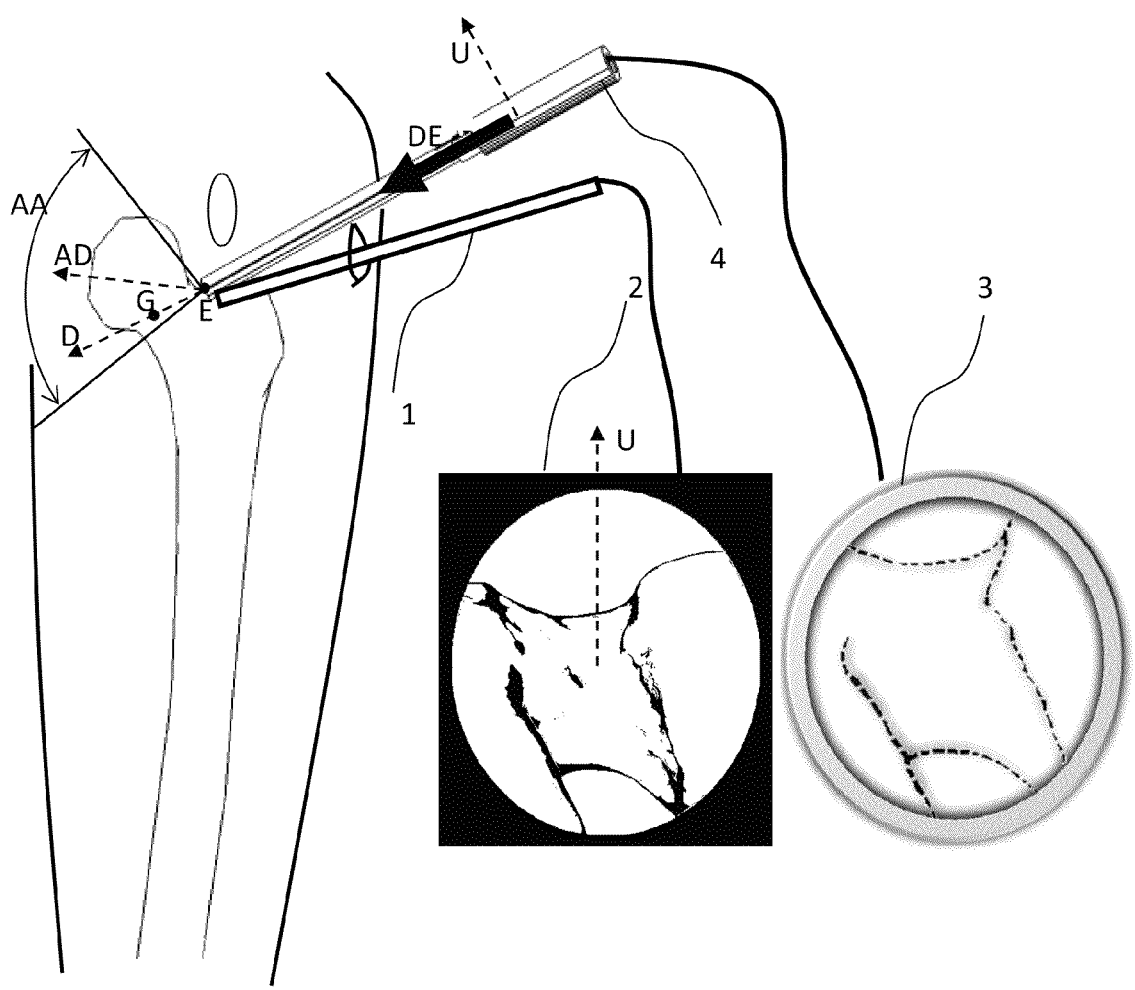
FIG. 9 is a schematic view of an embodiment of the method

The method described above is useful to provide a rehearsal and training tool to the users, including the surgeon, the medical staff, the students or even the patient. Indeed, once the portals have been determined in the 3D image, simulated arthroscopic images are now computed to provide the user with a theoretical vision of what will be seen by the arthroscope if the arthroscope was positioned precisely at the portals positions. During surgery, a real arthroscope 1 produces a real arthroscopic image 2. A virtual model 4 is then created to describe the existing arthroscope 1. It is assumed that the arthroscope is known in its entire geometry. Conventional calibration methods can be used to measure the parameters of an arthroscope. As shown in FIG. 9, the extremity of the arthroscope is E and its axis direction is DE. The optical axis direction AD is supposed to be known, it is not necessarily coincident with the arthroscope mechanical axis DE. The angle of visibility of the arthroscope AA is also known. To simulate the arthroscopic image that corresponds to a particular portal defined by a target point G and a direction D, the mechanical axis DE of the virtual arthroscope 4 is aligned with the portal direction D defined above. The arthroscope extremity E is placed on the portal direction D at a given distance d=(G,E) from the target point G defined above. The distance d can be a variable parameter that represents a simulation of the distance between the arthroscope extremity and the bone. A vertical direction U of the arthroscopic image is chosen arbitrarily. In practice, the user often turns a wheel on the arthroscope to vary the vertical direction U of the arthroscopic image. It is then possible to compute a virtual arthroscopic image 3 of the bone corresponding to this configuration from the 3D image using conventional ray-tracing visualization methods applied to the surface model of the bone S. The virtual arthroscopic image shows a simulation of what the arthroscope would see, including a projection of the bone surface model and any other features attached to the model. The light source is only one and it is emanating from the extremity E which makes simple and efficient lightening computations. For a given portal, the user can play with the distance parameter d which acts like a zoom and with a rotation around the axis DE to simulate what will be visible and check that a good visibility of the surgical area has been obtained. It provides a useful training and educational tool but also a rehearsal tool before surgery.

Figure 10:
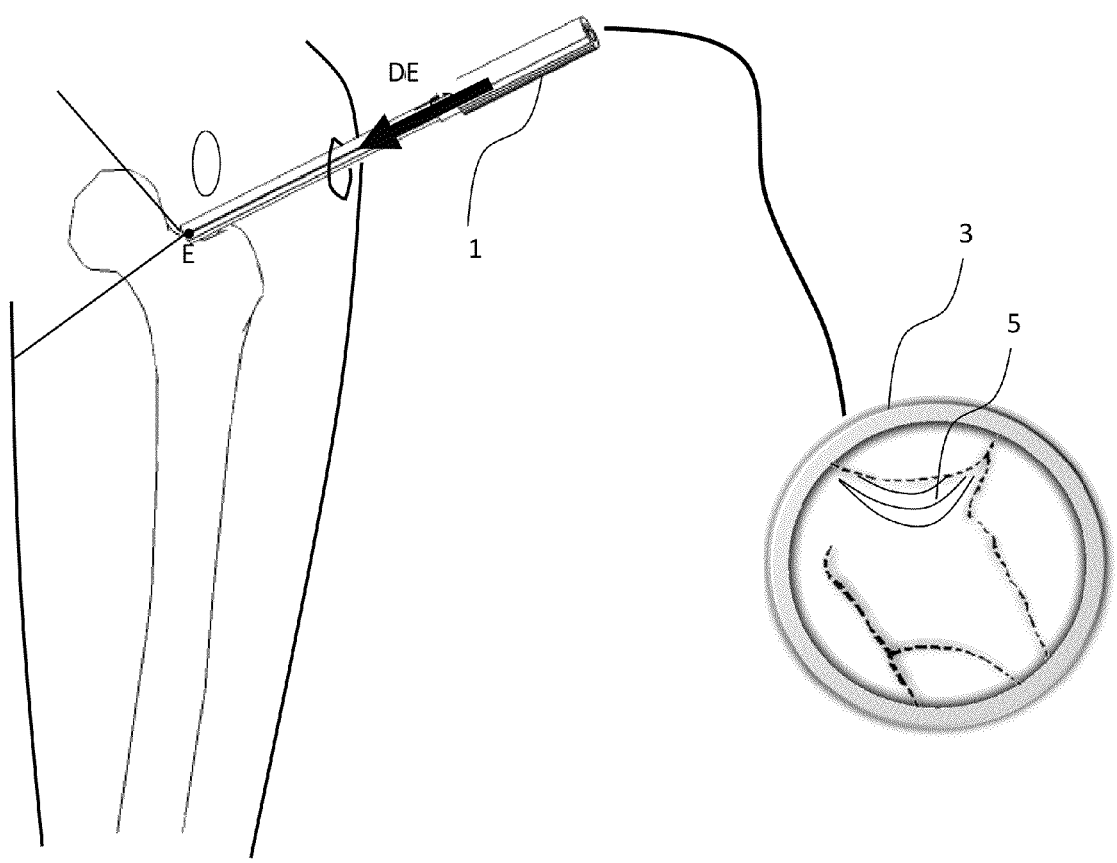
FIG. 10 is a schematic view of another embodiment of the method with a virtual arthroscopic image

In a preferred embodiment, surgical target areas are defined in the patient images. In FAI procedures, a surgical target is a resection volume that needs to be milled to recreate a normal surface of the bone. The method for determining the surgical target as an optimal surface is not in the scope of this invention since it is specific to the procedure and the optimization criteria. It is assumed that an optimal 3D resection volume has been defined, and which can be represented by a color map 5 with different colors corresponding to depth of bone to be milled, for instance green between 0 and 1 mm, yellow for depth between 1 and 2 mm, orange between 2 and 3 mm and the like. This color map 5 is superimposed to the bone surface model S. As shown in FIG. 10, the virtual arthroscopic image 3 contains not only the projection of the surface model but also a projection of the color map 5. Therefore, the user can check that the portal placement leads to a good visualization of the surgical target area. This process is repeated for all portals.

If the portals defined using the automated method described above are not providing a sufficient visibility of the surgical target area, the portal placements are modified interactively by the user using a mouse, around their initial position. It is then always possible to switch back to the initial position if erroneous displacements have been performed since the selection of portals is a very sensitive procedure.

The method described above can be used for calculating and displaying the virtual images before the surgery as a rehearsal tool, on a desktop in the surgeon office. But the memory of this simulation is then partially lost when the surgeon goes to the operating room. In a preferred embodiment, the virtual arthroscopic image 3 is displayed side by side to the real arthroscopic image 2, during a surgical procedure. Two dedicated monitors are used to display side by side the real and the virtual arthroscopic images. The user can have knowledge of the portal that corresponds to each virtual image since the portal direction D and target G can be displayed on one of the monitors as a reminder. When the user places a portal, it is recommended that the user places the portal according to the selected position which is displayed on the monitor. The visualization of the surgical target area on a virtual arthroscopic image which is quite similar to the real arthroscopic image brings significant information to the surgeon during the operation. The difference between the real and the virtual image can be interpreted mentally by the user and the user can try to move the real arthroscope until it matches the virtual arthroscopic image.

However, because of approximate placement due to the absence of any precise landmarks on the patient skin, the real portal and arthroscope direction 1 may not reach the desired position of the virtual arthroscope 4 precisely. The difference between the virtual and the real arthroscopic images can lead to frustration. In a preferred embodiment, a device is then added to determine a displacement of the virtual arthroscope 4. Such device can be any device such as a mouse, a joystick, a touch pad or buttons on touch screen, in order to generate a motion in two directions to create rotations of the virtual arthroscope around its initial axis and another motion in two directions to create a translation of the virtual arthroscopic image 3 in the image plane and another motion to generate a zoom effect. The rotation around the center of the image can be achieved on the real athroscopic image by using the wheel that controls the image rotation U on any conventional arthroscope. The user can manipulate those buttons if they are sterile, under sterile transparent draping for instance, or the user can ask an assistant to adjust those parameters for matching the virtual arthroscopic image with the real arthoscopic image whilst the real arthroscope stays still.

Figure 11:
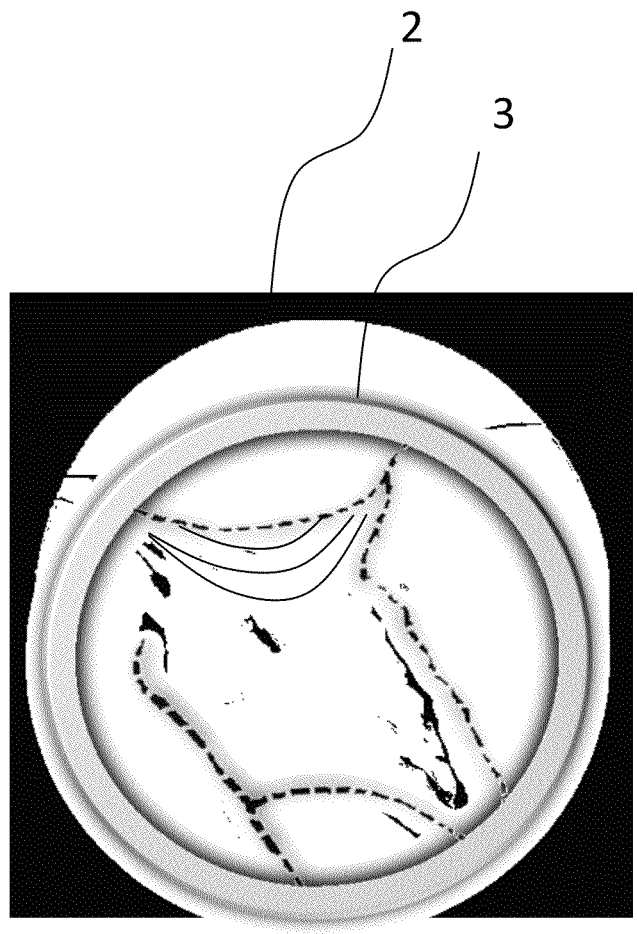
FIG. 11 is a schematic view of another embodiment of the method with a real arthroscopic image and a virtual arthroscopic image superimposed

In another embodiment, the adjustment of the virtual and the real arthroscopic images is automatically performed. The real arthroscopic image is digitized in real time in a computer video frame grabber. At that stage, the real arthroscopic image and the virtual arthroscopic image are quite similar thanks to the method described above. This is extremely important since it constitutes a good initial position for image registration. A conventional 3D to 2D image registration algorithm can then be used to adjust the position and orientation parameters of the virtual arthroscope until the real arthroscopic image and the virtual arthroscopic image have an optimal criterion such as entropy or mutual information. Those algorithms are prone to significant and frequent errors if the initial position of registration is too far and the images are too much different between themselves. The invention creates means to generate an initial registration transform that is in the convergence domain of most standard 3D to 2D registration algorithms. Usually, criteria based on a similarity function between the real and the virtual images are optimized according to the six parameters that define the position of the virtual arthroscope with respect to the coordinate system of the 3D image. Such criteria can be mutual information, the entropy, the correlation coefficient or the like. Having a good initial transform between the real and virtual images is also important to make the process fast enough so that the virtual image can track the real image in real time. Otherwise, the algorithm registers the images but lasts so long that meanwhile the user has moved the arthroscope and, thus, the real and virtual images never register together. Once the registration has been performed successfully for the first image, the resulting position is used as an initial position for the second registration and the method is iterated. If the tracking is lost, the initial transform computed using the method defined above is used again as a home position. Once registered, it is possible to superimpose the real and the virtual arthroscopic image as illustrated on FIG. 11. Therefore, the surgical targets are superimposed to the real arthroscopic images. Since the real arthroscopic image pictures the instruments, the tip of an instrument is now superimposed to the surgical target. The superimposition can be implemented using a variable transparency effect. It is important to note that this method does not necessitate any navigation device. A conventional computer equipped with a video frame grabber is sufficient.

Figure 12:
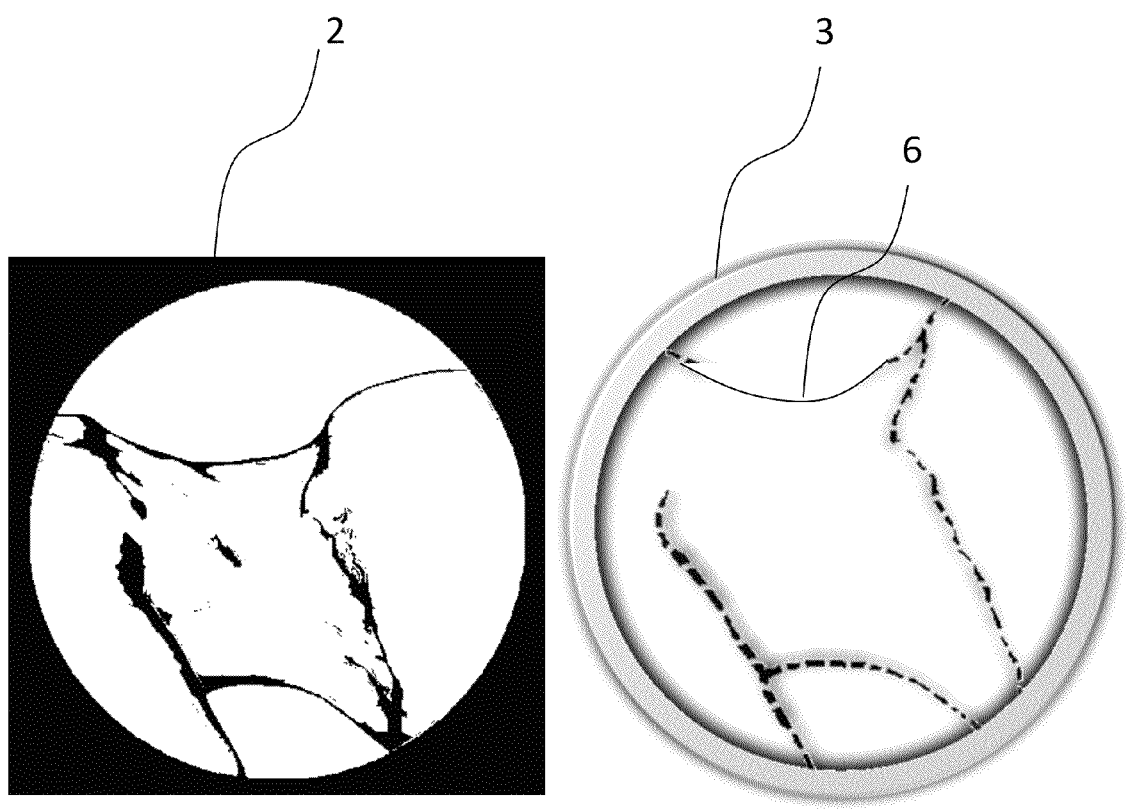
FIG. 12 is a schematic view of another embodiment of the method with a real arthroscopic image and a virtual arthroscopic image side by side.

In another embodiment, as shown in FIG. 12, the surgical target area is represented directly by a single color surface patch 6 to be achieved after resection. The single color surface patch 6 represents an optimal surface to be milled after surgery and only the area to be milled is colored. The surface model of the patient is then replaced by this optimally milled surface in the method described above. In a preferred embodiment, the real arthroscopic image 2 and the virtual arthroscopic image 3 are displayed side by side such that the user can make a comparison of the edges and mill the bone until both images are similar. This method can be used in alternation with the color map method displayed above such that the user can see at any time the objective represented by an optimally milled surface and also the path to reach the objective represented by a color map.

Furthermore, intra-operatively, if the patient images are registered to the patient coordinate system using one of the numerous image-guided surgery registration methods, then the characteristic elements built in Rbone are determined in the intra-operative patient coordinate system Rop which is usually attached to a tracker localized in three dimensions using an optical or magnetic system. Using a navigation, haptic or robotic device, the user can use the position of such characteristic elements in correlation with the surgical instruments in order to place the instruments at the precisely defined portal locations whilst avoiding the dangerous areas. In addition, intra-operative data can be used in the method to reinforce the accuracy of the location of characteristic elements. Such intra-operative data can be landmarks points collected using a navigation system during the surgical procedure once the patient registration has been performed.

Advantages

The advantage of the exposed method is to determine with accuracy and automatically characteristic access elements from patient 3D images. These elements are surgical access planning elements useful in case arthroscopy procedures. The method is useful to rehearse the surgery and also for training and education purpose. In addition, the method makes it possible to register virtual arthroscopic images with real arthroscopic images such that surgical targets defined on 3D images can be visible on real images without using expensive navigation devices.

The invention claimed is:

1. A method for automatically determining at least one pre-operative portal for arthroscopy from acquired pre-operative medical images of a bone of a patient, said method comprising the following steps:
   i) constructing a 3D surface of the bone from the 3D image of the bone;
   ii) automatically determining anatomical landmarks of the bone from the 3D surface;
   iii) determining a bone reference coordinate system from the anatomical landmarks;
   iv) selecting at least one predetermined portal in a database of positions of predetermined portals previously defined on a 3D model representing a bone of a reference person, wherein the database of positions of predetermined portal comprises a data base of arthroscopic portals defined by a tool entry point and a direction for each of the arthroscopic portals;
   v) determining a transform between the bone reference coordinate system and the model coordinate system so that the bone of the patient represented in the bone reference coordinate system and the bone of the reference person represented in the model coordinate system are matched in size, in position and/or shape; and
   vi) inferring from the transform and the at least one predetermined portal the preoperative portal.

2. A method for simulating arthroscopic Images before surgery, comprising the steps of
   determining at least one pre-operative portal by the method of claim 1,
   placing a virtual arthroscope at said pre-operative portal and
   computing a virtual arthroscopic Image of the surgical area obtained by the virtual arthroscope.

3. The method of claim 1, wherein the pre-operative portal is an arthroscopic portal defined by a tool entry point and a direction.

4. The method of claim 1, further comprising inferring through the transform critical areas containing vessels or nerves from the model coordinate system to the bone reference coordinate system.

5. The method of claim 1, wherein the transform is determined through analytical and/or geometric process.

6. The method of claim 1, wherein the transform is determined as a continuous function from the model coordinate system to the bone reference coordinate system.

7. The method of claim 6, wherein the transform is determined through a non-rigid image-to-image or surface-to-surface registration algorithm.

8. The method of claim 2, wherein the pre-operative portal is an arthroscopic portal defined by a tool entry point and a direction, and wherein a virtual arthroscopic image is constructed from the arthroscopic portal.

9. The method of claim 8, further comprising generating planning information and superimposing the planning information onto the virtual arthroscopic image.

10. The method of claim 9, wherein planning information is a color map representing amount of bone to be removed.

11. The method of claim 9, wherein planning information is a projection of an optimal surface to be built onto the bone.

12. The method of claim 8, further comprising generating an adjusted virtual arthroscopic image by adjusting and registering the virtual arthroscopic image to real arthroscopic image of the bone.

13. The method of claim 12, wherein registering the virtual arthroscopic image to real arthroscopic image of the bone comprises the following steps:
   i) initial registration by using the inferred portal position;
   ii) adjustment of registration using image to image registration.

14. The method of claim 12, further comprising generating planning information and generating a superimposed image by superimposing the planning information onto the adjusted virtual arthroscopic image.

15. The method of claim 12, further comprising generating planning information and superimposing planning information and the adjusted virtual arthroscopic image onto the real arthroscopic image of the bone.

16. The method of claim 14, further comprising displaying the superimposed image and the real arthroscopic image side by side.

17. The method of claim 1, further comprising the manual modification of the pre-operative portal around its initial computed position.

* * * * *